US011840715B2

(12) United States Patent
Nguyen et al.

(10) Patent No.: US 11,840,715 B2
(45) Date of Patent: Dec. 12, 2023

(54) MICROELECTRODE ARRAY WITH A SWITCHABLE HYDROPHILIC SURFACE

(71) Applicant: MICROSOFT TECHNOLOGY LICENSING, LLC, Redmond, WA (US)

(72) Inventors: Bichlien Nguyen, Seattle, WA (US); Jake Smith, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 505 days.

(21) Appl. No.: 16/917,650

(22) Filed: Jun. 30, 2020

(65) Prior Publication Data

US 2021/0403968 A1 Dec. 30, 2021

(51) Int. Cl.
| | |
|---|---|
| C12P 19/34 | (2006.01) |
| B01L 7/00 | (2006.01) |
| C07H 1/00 | (2006.01) |
| C07H 21/04 | (2006.01) |
| C12Q 1/6844 | (2018.01) |
| C25D 9/02 | (2006.01) |

(52) U.S. Cl.
CPC ............... *C12P 19/34* (2013.01); *B01L 7/525* (2013.01); *C07H 1/00* (2013.01); *C07H 21/04* (2013.01); *C12Q 1/6844* (2013.01); *C25D 9/02* (2013.01); *B01L 2200/16* (2013.01); *B01L 2300/123* (2013.01); *B01L 2300/165* (2013.01)

(58) Field of Classification Search
CPC ...... C12P 19/34; B01L 7/525; B01L 2200/16; B01L 2300/123; B01L 2300/165; B01L 2300/0819; B01L 2400/0427; B01L 2400/082; B01L 3/502792; C07H 1/00; C07H 21/04; C12Q 1/6844; C12Q 1/001; C25D 9/02
See application file for complete search history.

(56) References Cited

U.S. PATENT DOCUMENTS 4,721,601 A 1/1988 Wrighton et al.

FOREIGN PATENT DOCUMENTS

| WO | 9967628 A1 | 12/1999 |
| WO | 0131057 A2 | 5/2001 |
| WO | 2015191924 A1 | 12/2015 |

OTHER PUBLICATIONS

Kittlesen et al, A Microelectrochemical Diode with Submicron Contact Spacing Based on the Connection of Two Microelectrodes Using Dissimilar Redox Polymers, 1985, J. Am. Chem. Soc., 107, 7373-7380. (Year: 1985).*

Viswam et al, High-Density Mapping of Brain Slices using a Large Multi-Functional High-Density CMOS Microelectrode Array System, Int Solid State Sens Actuators Microsyst Conf. Jun. 2017 ; 2017: 135-138. (Year: 2017).*

Gras, et al., "Intelligent Control of Surface Hydrophobicity", In Journal of ChemPhysChem, vol. 8, Issue14, Oct. 8, 2007, pp. 2036-2050.

"International Search Report and Written Opinion Issued in PCT Application No. PCT/US2021/031468", dated Aug. 27, 2021, 11 Pages.

Chmielewski, Marcin K., "Novel Thermolabile Protecting Groups with Higher Stability at Ambient Temperature", Published in Journal Tetrahedron Letters vol. 53, Issue 6, Feb. 8, 2012, pp. 666-669.

Egeland, et al., "Electrochemically Directed Synthesis of Oligonucleotides for DNA Microarray Fabrication", In Journal of Nucleic Acids Research, vol. 33, Issue 14, Aug. 5, 2005, pp. 1-7.

Elbert, et al., "Ferrocene Polymers for Switchable Surface Wettability", Published in Journal of Organometallics, vol. 32, Issue 20, Jun. 21, 2013, pp. 5873-5878.

Gabriel, et al., "Thermoresponsive Coatings Strongly Adhering to (Semi)conducting Surfaces", Published in Journal of Langmuir, vol. 23, Issue 1, Jan. 2007, pp. 159-161.

Hirao, et al., "Recent Advance in Living Anionic Polymerization of Functionalized Styrene Derivatives", Published in Journal of Progress in Polymer Science, vol. 27, Issue 8, Oct. 1, 2002, pp. 1399-1471.

Le, et al., "Improved PCR flexibility with Hot Start dNTPs", Published in Journal of BioTechniques, vol. 47, Issue 4, Oct. 2009, pp. 881-882.

Li, et al., "Amphiphilic Block Copolymers of Polyvinyl Alcohol and Polystyrene and Their Surface Properties", Published in Polymer Journal, vol. 37, Issue 11, Nov. 2005, pp. 841-846.

Liu, et al., "Maskless Hydrophilic Patterning of the Superhydrophobic Aluminum Surface by an Atmospheric Pressure Microplasma Jet for Water Adhesion Controlling", Published in Journal of ACS Applied Materials & Interfaces, vol. 10, Issue 8, Feb. 28, 2018, pp. 7497-7503.

Martinez-Rivas, et al., "Methods of Micropatterning and Manipulation of Cells for Biomedical Applications", Published in Journal of Micromachines, vol. 8, Nov. 29, 2017, pp. 1-20.

Seuring, et al., "Polymers with Upper Critical Solution Temperature in Aqueous Solution", Published in Journal of Macromolecular Rapid Communications vol. 33, Issue 22, Nov. 23, 2012, pp. 1898-1920.

(Continued)

*Primary Examiner* — Narayan K Bhat
(74) *Attorney, Agent, or Firm* — Newport IP, LLC; Benjamin A. Keim

(57) ABSTRACT

A switchable hydrophilic surface is created by attaching electrochemically switchable hydrophilicity polymers to the surface of a microelectrode array. Ferrocene polymers are one example of electrochemically switchable hydrophilicity polymers. Activation of electrodes in the microelectrode array changes the oxidation state of metal ions which switches the polymers between hydrophobic and hydrophilic conformations. Selective activation of electrodes can create patterns of wettability on the microelectrode array that may be varied in real time. The switchable hydrophilic surface may be used to control solid-phase synthesis of polymers. Growing polymers may be selectively extended at locations on the microelectrode array that are hydrophilic. The pattern of hydrophobic and hydrophilic regions can be changed during sequential rounds of synthesis to create a variety of different polymers at different locations on the surface of the microelectrode array.

18 Claims, 9 Drawing Sheets

(56) References Cited

OTHER PUBLICATIONS

Snapp, et al., "Interaction of 2D Materials with Liquids: Wettability, Electrochemical Properties, Friction, and Emerging Directions", Published in Journal NPG Asia Materials vol. 12, Issue 1, Mar. 13, 2020, pp. 1-16.

Qu, et al., "Aminoazobenzene@Ag Modified Meshes With Large Extent Photo-Response: Towards Reversible Oil/ Water Removal From Oil/Water Mixtures", Published in Journal of Chemical Science, vol. 10, Issue 14, Feb. 25, 2019, pp. 4089-4096.

Wagner, et al., "Light-Induced Wettability Changes on Polymer Surfaces", Published in Journal Polymer, vol. 55, Issue 16, Aug. 5, 2014, pp. 3436-3453.

Wang, et al., "High-Strength Photoresponsive Hydrogels Enable Surface-Mediated Gene Delivery and Light-Induced Reversible Cell Adhesion/ Detachment", Published in Journal Langmuir, vol. 30, Issue 39, Oct. 7, 2014, pp. 11823-11832.

Wang, et al., "Photoresponsive Surfaces with Controllable Wettability", In Journal of Photochemistry and Photobiology C: Photochemistry Reviews, vol. 8, Issue 1, Mar. 12, 2007, pp. 18-29.

\* cited by examiner

MICROELECTRODE ARRAY WITH A SWITCHABLE HYDROPHILIC SURFACE

BACKGROUND

Microarrays and their surfaces are often patterned before use. For example, the patterned flow cells used in sequencing-by-synthesis technology are patterned with geometry that defines the locations where oligonucleotides are bound during the sequencing process. The patterning is achieved by etching nanowells in glass. Microarrays may also be patterned by techniques such as photolithography which use a mask to create a pattern or by spotting which uses a robot to "print" molecules at specific locations. Once a flow cell is etched or a microarray is patterned, the pattern cannot be altered unless the patterning is stripped from the surface and a new pattern is created.

Digital microfluidic (DMF) systems can move droplets by changes in electric currents. DMF systems may be open or closed. In an open system a droplet sits on top of a surface with a patterned array of individually controllable electrodes. The surface, often glass, may be coated with a hydrophilic material. Electrowetting moves the droplet across the surface by varying the electric potential of adjacent electrodes and making the droplet polarized. A closed system has a top layer that usually contains a ground electrode and may be uniformly coated with a hydrophobic layer. The electric potential of the electrodes changes but the hydrophilic and hydrophobic characteristics of the surfaces do not change. DMF systems typically require over 100 volts to move a droplet.

Although microarrays and DMF systems can perform some tasks well, they are both difficult to adapt to new applications and cannot be customized in real time. The following disclosure is made with respect to these and other considerations.

SUMMARY

This disclosure provides a microelectrode array coated with electrochemically switchable hydrophilicity polymers. In an implementation, the electrochemically switchable hydrophilicity polymers may be ferrocene polymers such as polyvinylferrocene (PVFc) or poly(2-(methacryloyloxy) ethyl ferrocenecarboxylate) (PFcMA). The microelectrode array may be any type of microelectrode array such as a complementary semiconductor-metal-oxide (CMOS) microelectrode array. The polymers can be switched between a hydrophobic conformation and a hydrophilic conformation by activation of the microelectrode array through a change in the oxidation state of metal ions. This arrangement creates a surface with wettability that can be spatially controlled and changed. The wettability gradient drives patterning of a liquid in contact with the surface of the microelectrode array.

In an implementation, the microelectrode array coated with the electrochemically switchable hydrophilicity polymers may be used for solid-phase synthesis of other polymers such as deoxyribose nucleic acid (DNA). Synthesis occurs at the locations where a reaction mixture is retained which are the hydrophilic regions on the surface of the microelectrode array. This may also be used to control the deposition of biological material such as in tissue engineering or cell patterning applications. Functional handles for starting the synthesis of polymers may be provided on the electrochemically switchable hydrophilicity polymer or on the surface of the microelectrode array. For example, oligonucleotides may be the functional handles for synthesis of DNA.

During a round of solid-phase synthesis, monomers are added only to those regions of the microelectrode array that are hydrophilic. A reagent solution that contains the monomers (e.g., nucleotides for synthesis of DNA) collects at the hydrophilic areas but flows off of the hydrophobic areas. Alternatively, a deblocking solution may remove protecting groups that prevent polymerization only from those regions of the microelectrode array that are hydrophilic. The pattern of hydrophobic and hydrophilic regions can be repeatedly changed leading to incorporation of monomers at different areas of the microelectrode array in different rounds of synthesis. The type of monomer added (e.g., a single species of deoxynucleoside triphosphate (dNTP)) may also be changed during each round of synthesis. This enables synthesis of a population of polymers with different sequences on the surface of the microelectrode array.

A system for solid-phase synthesis that uses this microelectrode array coated with electrochemically switchable hydrophilicity polymers includes multiple fluid delivery pathways for bringing various fluids into contact with the surface of the microelectrode array such as an electrolyte solution, a reagent solution, and a wash solution. The system also includes a device for clearing fluid from the surface of the microelectrode array such as by spin drying or blow drying. Control circuitry may control the activation of electrodes in the microelectrode array and the opening of fluid delivery pathways to create polymers on the surface of the microelectrode array with specific sequences.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Elements shown in the figures are schematic and not to scale.

DETAILED DESCRIPTION

Figure 1:
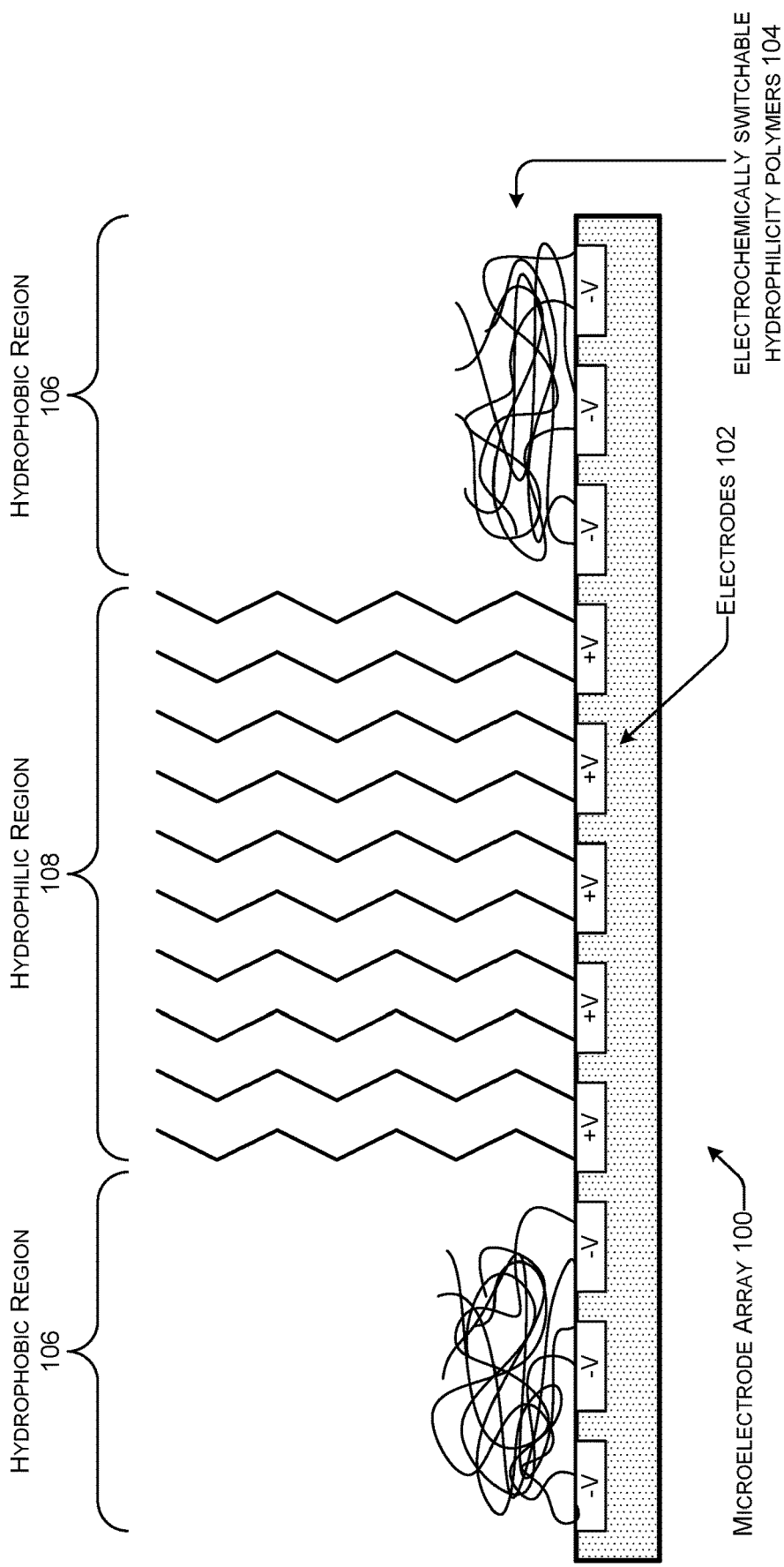
FIG. 1 is a schematic diagram of a microelectrode array coated with electrochemically switchable hydrophilicity polymers.

This disclosure provides techniques and systems that use a microelectrode array coated with electrochemically switchable hydrophilicity polymers to create a surface with switchable hydrophilicity that can be controlled in real time by selective activation of electrodes in the microelectrode array. Electrochemically switchable hydrophilicity polymers are molecules that can change between a conformation that is hydrophilic and a conformation that is hydrophilic. One type of polymers with this property are polyvinylferrocene polymers.

Polyvinylferrocene polymers include PVFc and PFcMA which are redox responsive polymers that contain ferrocene moieties that, when oxidized, increase hydrophilicity and swelling of the resulting polyelectrolyte. Both PVFc and PFcMA are known to undergo a fast and reversible redox reaction accompanied by a local change of polarity and a remarkable swelling behavior after oxidation of the ferrocene moieties. Characteristics of these polymers are described in Songul Sen Gursoy et al., *Synthesis and Characterization of Polyvinylferrocene/Polypyrrole Composites*, 45(6) J. of Macromolecular Sci. 485 (2008). Songul et al. describe chemical oxidation of the ferrocene moieties with iron(III) chloride ($FeCl_3$) or tris(4-bromophenyl)ammoniumyl hexachloroantimonate ($(BrC_6H_4)_3NSbCl_6$)) not with a microelectrode array.

Creating a negative voltage on electrodes in a microelectrode array can cause a redox reaction that changes polyvinylferrocene polymers to a hydrophobic conformation. Conversely, applying a positive voltage can change the polyvinylferrocene polymers to a hydrophilic conformation. Use of a microelectrode array provides a non-chemical and spatially-addressable way to selective create a pattern of hydrophobic and hydrophilic regions on the surface of the microelectrode array. The pattern of wettability may also be readily changed by changing the pattern of electrode activation.

The techniques, methods, systems, and devices of this disclosure may also be adapted to work with different types of polymers that change confirmation in response to changes in conditions other than electrochemistry. One example of such polymers are thermoresponsive polymers that change swelling properties in response to temperature. When expanded, thermoresponsive polymers enter solution and any functional groups attached to the polymers are available to participate in reactions. When contracted, the polymers collapse over themselves and cover any functional groups making them unavailable.

The surface of a microelectrode array containing individually controlled resistors may be coated with thermoresponsive polymers by techniques such as electrografting. Specific resistors in the array can be activated and heat the thermoresponsive polymers and aqueous solution to a specific temperature in a patterned fashion. This patterning may be used to control polynucleotide synthesis. The thermoresponsive polymers may be cooled to ambient temperature by turning off resistors and allowing the temperature to equilibrate. A cold aqueous wash solution may also be used to lower the temperate of the thermoresponsive polymers. Other techniques such as laser heating or ultrasound may also be used to create spatially-addressable heating on the surface of an array.

Some thermoresponsive polymers become hydrophobic, immiscible with aqueous solution, and collapse at elevated temperatures. This type of thermoresponsive polymer exhibits lower critical solubility temperature (LCST) behavior. One example is modified poly(N-isopropyl acrylamide) (PNIPAM) scaffolds. The structure and general properties of these polymers are described in Sabine Gabriel, *Thermoresponsive Coatings Strongly Adhering to (Semi) conducting Surfaces*, 23 Langmuir 159 (2007). At temperatures greater than 42° C. PNIPAM collapses to under 10 nm. At room temperature and cooler, PNIPAM is hydrophilic, miscible with water, and swells to about 80 nm.

Other thermoresponsive polymers become water-miscible and enter solution at elevated temperatures. This type of thermoresponsive polymer exhibits upper critical solubility temperature (UCST) behavior. One example is poly(uracilacrylate) (PAU) which becomes water-miscible at temperatures above 60° C. PAU and other UCST polymers are described in Jan Seuring and Seema Agarwal, *Polymers with Upper Critical Solution Temperature in Aqueous Solution*, 33 Macromol. Rapid Commun. 1898 (2012).

UCST polymers may be used together with enzymes that have elevated activation temperatures for polynucleotide synthesis. For example, HiFi Taq DNA ligase is active between 35° C. to 75° C. with typical ligations at a working temperature of 60° C. This is the same temperature that PAU becomes hydrophilic and enters solution. Other "hot-start" enzymes may also be used. Using a thermoresponsive polymer that exhibits UCST behavior in combination with a heat activated enzyme can improve confinement for parallel polynucleotide synthesis by 1) controlling location of polymers that make functional groups are available and 2) activating enzymes only at locations where the polymers are extended and the functional groups are available for synthesis. In some implementations, nucleotides used for polynucleotide synthesis may include a thermally labile protecting group which must be heated to a specific temperature range to be removed. This adds a third layer of selectivity that controls where nucleotides may be added to growing polynucleotide strands. Examples of thermolabile protecting groups are provided in Marcin Chmielewski, *Novel thermolabile protecting groups with higher stability at ambient temperature*, 53 Tetrahedron Letters 666 (2012).

Thermoresponsive polymers may be synthesized so that the polymers themselves include functional handles for attachment of other types of molecules including other polymers such as polynucleotides. The function handles generally include a reactive group such as acrylic acid or any of the other reactive groups described in this disclosure. Thermoresponsive polymers that include functional handles can be created by any one of a number of synthetic techniques that combine monomer subunits of the thermoresponsive polymers with other monomer units that include a functional handle. Suitable techniques are known to persons of ordinary skill in the art and include random copolymerization, block copolymerization, and living polymerization.

For polynucleotide sequencing or synthesis, thermoresponsive polymers provide a novel method to control the ability to spatially isolate the polynucleotide polymerization process on the surface of an array in real-time. The polymer that acts as the surface of the array can be tuned to be hydrophobic (i.e., collapsed state hiding any functional groups) or hydrophilic (i.e., swollen state exposing the functional groups) in solution by changing the local temperature. A collapsed thermoresponsive polymer will not support polynucleotide synthesis while a thermoresponsive polymer in a swollen state will. Additionally, this modulation control of the surface can be coupled with enzymatic synthesis to provide dual control by controlling both the temperature activation of the enzyme and swellability of the polymers.

Another type of polymers that may be used with the techniques of this disclosure are photoresponsive polymers. Photoresponsive polymers can reversibly switch between hydrophobic and hydrophilic configuration in response to exposure to light. There are many known types of photoresponsive polymers that can change wettability. See Shutao Wang et al., *Photoresponsive surfaces with controllable wettability*, 8 J. Photochem. and Photobio. 18 (2007) (describing azobenzenes, spiropyrans, and cinnamates); Natalie Wagner, and Patrick Theato, *Light-induced wettability changes on polymer surfaces,* 55 Polymer 3436 (2014) (describing azobenzene, spiropyran, cinnamate, polysulfone, polyethersulfone, diarylethene, diethylcyclopentene-based self-assembled monolayers, and coumarin-functionalized surfaces); Ning Wang et al., *High-Strength Photoresponsive Hydrogels Enable Surface-Mediated Gene Delivery and Light-Induced Reversible Cell Adhesion/Detachment,* 30 Langmuir 11823 (2014) (describing photoresponsive hydrogels); and Ruixiang Qu et al., *Aminoazobenzene@Ag modified meshes with large extent photo-response: towards reversible oil/water removal from oil/water mixtures,* 10 Chem. Sci. 4089 (2019) (describing aminoazobenzene).

One illustrative type of photoresponsive polymer, spiropyran polymers, become hydrophilic by exposure to 365 nm UV light and can be returned to a hydrophobic conformation by exposure to about 500 nm visible light. Another type of photoresponsive polyer, azobenzene polymers, also become hydrophilic by exposure to 365 nm UV light and can be returned to a hydrophobic conformation by exposure to 494 nm visible light. Spatially-addressable patterning of these and other photoresponsive polymers may be created by controlled exposure to light such as by use of a photomask, digital micro mirror (DMM), or other technique known in the art including techniques used for patterning of integrated circuits.

Photoresponsive polymers may include a polyvinyl chain as the backbone, the same backbone as polyvinylferrocene polymers. Similar modifications may be made to photoresponsive polymers as to polyvinylferrocene polymers such as additional of functional handles. Any of the functional handles used with polyvinylferrocene polymers may also be used with photoresponsive polymers. In some implementations, acrylic acid may be used as a functional handle or as a functional block that is incorporated during polymer synthesis.

A substrate may be functionalized with photoresponsive polymers by any number of techniques known to those of skill in the art. The specific technique will depend to the substrate and the type of photoresponsive polymer. Any of the techniques discussed elsewhere in this disclosure such as random copolymerization, block copolymerization, and capping of a living polymer may be used. The photoresponsive polymers may be generated in situ using a surface-bound initiator on the substrate or generated in solution and grafted onto the substrate. For example, spiropyran polymers and azobenzene polymers may both be grafted onto a substrate to create dense polymer brushes using atom transfer radical polymerization (ATRP).

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1 shows a schematic diagram of a microelectrode array 100 containing a plurality of electrodes 102. The surface of the microelectrode array 100 is coated with electrochemically switchable hydrophilicity polymers 104 such as, but not limited to, polyvinylferrocene polymers.

The microelectrode array 100 is an array that contains many small, spatially addressable electrodes 102. The electrodes 102 may be formed from a metal such as gold or another metal plated with gold. Each electrode may be individually connected to a printed circuit board that may be controlled by a computer. In an implementation, the microelectrode array 100 may be constructed in whole or part from a silicon dioxide wafer. Thus, all or part of the surface of the microelectrode array 100 may be a substantially flat silicon dioxide surface.

In one implementation, the microelectrode array 100 may be created by positive resist photolithography to produce, for example, iridium metal electrodes on oxidized high-resistivity silicon wafers. In some implementations, the microelectrode array 100 may be an integrated circuit (IC) constructed using complementary metal-oxide-semiconductor (CMOS) technology. The CMOS may include metal-oxide-semiconductor field-effect transistors (MOSFETs) made through a triple-well process or by a silicon-on-insulator (SOI) process. A series of controllable gates/transistors implemented with CMOS circuits can be controlled to inject charge at any location on the surface of the microelectrode array 100. Each electrode 102 in the microelectrode array 100 may be independently addressed allowing the creation of arbitrary and variable voltage microenvironments across the surface of the microelectrode array 100.

High microelectrode density allows for fine-scale level control of the ionic environment at the surface of the microelectrode array. A microelectrode array may have a microelectrode density of approximately 1024 microelectrodes/$cm^2$, approximately 12,544 microelectrodes/$cm^2$, or a different density. Examples of microelectrode arrays are provided in Bo Bi et al., *Building Addressable Libraries: The Use of "Safety-Catch" Linkers on Microelectrode Arrays,* 132 J. Am. Chem. Soc. 17, 405 (2010), Bichlien H. Nguyen et al., *Microelectrode Arrays: A General Strategy for Using Oxidation Reactions To Site Selectively Modify Electrode Surfaces,* 30 Langmuir 2280 (2014), and U.S. patent application Ser. No. 16/435,363 filed on Jun. 7, 2019, with the title "Reversing Bias in Polymer Synthesis Electrode Array."

The electrochemically switchable hydrophilicity polymers 104 may be attached to the surface of the microelectrode array 100 by any number to techniques suitable for the specific polymer structure and the material on the surface of the microelectrode array 100. A person of ordinary skill in the art will be able to identify and implement an appropriate technique for anchoring electrochemically switchable hydrophilicity polymers 104 to the surface of a microelectrode array 100. In an implementation, PVFc may be attached by PVFc-TEOS grafting onto a silica wafer. In this technique, a dry silica wafer is contacted with dry toluene and PVFc-TEOS and heated to about 120° C. for about 24 hours. The silicon wafer can be extracted with THF to remove the physiosorbed polymer. In an implementation, FcMA may be grafted onto a silica wafer through surface-initiated atom transfer radical polymerization (SI-ATRP). SI-ATRP begins by attaching an initiator onto a dry silica wafer by contacting the silica wafer with dry toluene and 3-(2-bromoisobutyrate)propyl trichlorosilane then heating to about 60° C. for about 16 hours. The silicon wafers are then extracted with THF to remove physisorbed initiator. The silicon wafers functionalized with the initiators are contacted with anison, FcMA, and 2-bromoisobutyric tert-butyl ester then heating to about 90° C. for about 10 minutes. Polymerization is initiated by adding a solution of [CuI (PMDETA)-Cl]. See Songul et al. supra.

The characteristic of an electrochemically switchable hydrophilicity polymer 104 as hydrophobic or hydrophilic changes in response to activation of an electrode 102 in proximity to the location of the electrochemically switchable hydrophilicity polymer 104. Proximity, proximate, or similar referents as used in this context means close enough to the electrode 102 to change an oxidation state of a metal ion in response to a change of the electrode potential of the electrode 102.

Control of the charge at individual electrodes 102 can create any arbitrary pattern of one or more hydrophobic regions 106 and hydrophilic regions 108 on the surface of the microelectrode array 100. The hydrophobic regions 106 correspond to regions where the electrodes 102 have a negative charge. In a hydrophobic conformation the electrochemically switchable hydrophilicity polymers 104 collapse into a "crumpled" or non-regular structure. The hydrophilic regions 108 correspond to regions where the electrodes 102 have a positive charge. In a hydrophilic conformation the electrochemically switchable hydrophilicity polymers 104 are generally aligned and extended into solution. Once the electrochemically switchable hydrophilicity polymers 104 adopt a given conformation the hydrophilic or hydrophobic quality of the electrochemically switchable hydrophilicity polymers 104 remains after the electrodes 102 are turned off. The electrochemically switchable hydrophilicity polymers 104 will hold a conformation until a redox reaction changes the oxidation state of a metal ion such as a ferrocene moiety.

Figure 2:
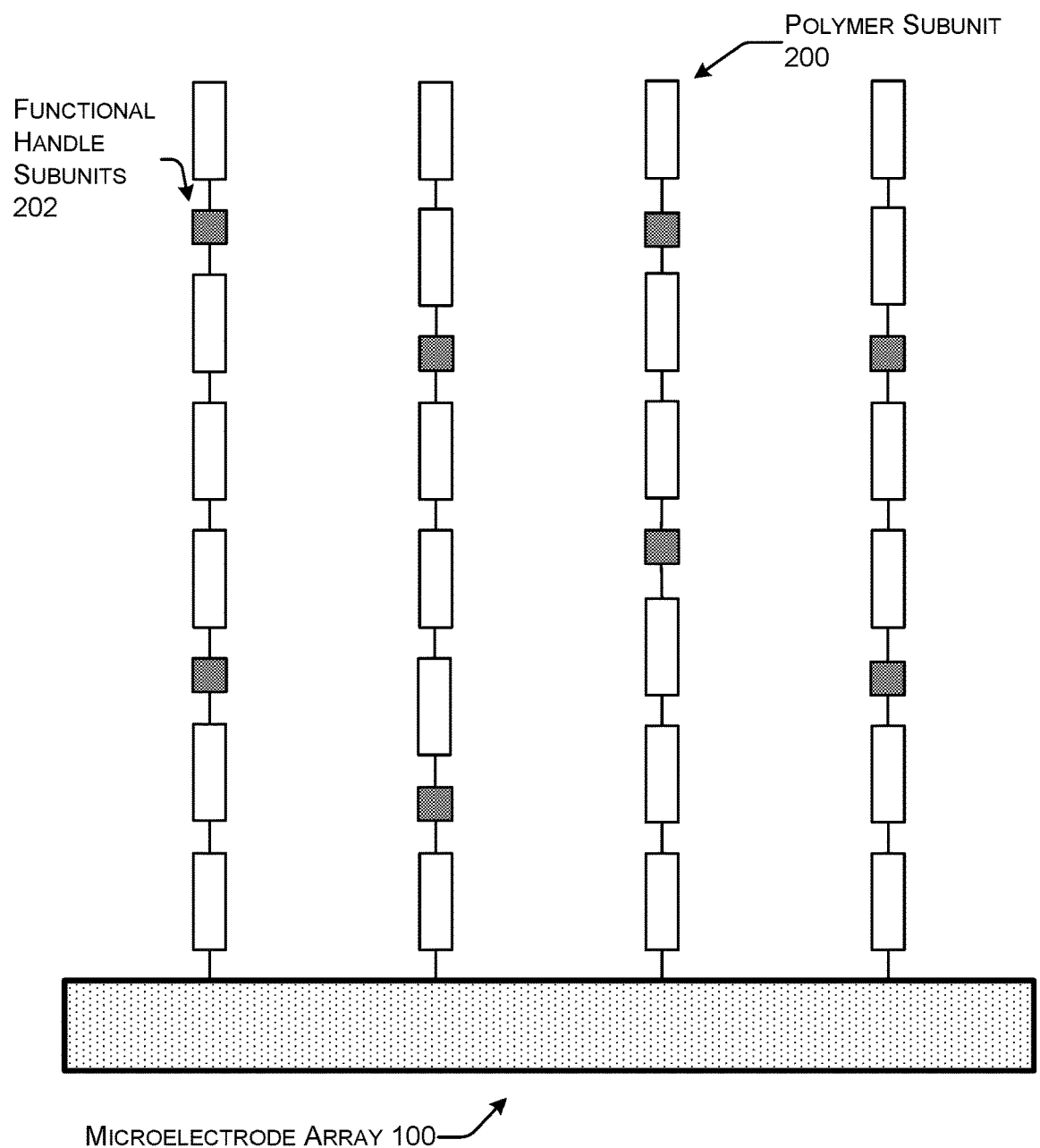
FIG. 2 is a schematic diagram of a microelectrode array coated with electrochemically switchable hydrophilicity polymers created by random copolymerization of polymer subunits and functional handle subunits.

FIG. 2 shows a microelectrode array 100 coated with electrochemically switchable hydrophilicity polymers 104 created by random copolymerization of polymer subunits 200 and functional handle subunits 202. The polymer subunits 200 are comprised of monomer subunits of any of the electrochemically switchable hydrophilicity polymers 104 described in this disclosure such as vinylferrocene monomers. The functional handle subunits 202 are comprised of monomers that include a functional group.

The functional handle subunits 202 provide an anchor or starting point for addition of monomers to create a polymer. The functional handle subunits 202 are used for growing polymers other than the electrochemically switchable hydrophilicity polymers 104. Each monomer subunit within functional handle subunit 202 will generally include a reactive group that is available for a polymerization reaction with a monomer subunit of the polymer to be formed or that is connected to a linker molecule that in turn is connected to a monomer subunit of the polymer to be formed. Examples of reactive groups include acrylic acid (also called propenoic acid), amino groups, carboxyl groups, esters, carbonyl groups, olefins, alkyne groups, azide groups, and alcohols. Examples of linkers include polyethylene glycol (PEG) or similar non-reactive molecules. In an implementation, an acrylic acid functional handle may be connected with a linker that provides an amine functionality through a primary, secondary, or tertiary amine. Oligonucleotide sequences are an additional example of a monomer subunit that may be connected to a functional handle subunit 202. Polynucleotide synthesis may be initiated by adding nucleotides to the end, generally the 3'-end, of an existing oligonucleotide. The oligonucleotide sequence may be a single nucleotide or longer such as sequences of 2-20 nucleotides. The type of functional group may be selected based on the polymer that will be synthesized and the specific synthetic technique used.

Random copolymer synthesis may be performed in situ on the surface of the microelectrode array 100. Alternatively, the electrochemically switchable hydrophilicity polymers 104 with functional handle subunits 202 may be pre-synthesized by copolymer synthesis and attached to the surface of the microelectrode array 100.

Random copolymers comprise two or more monomer subunits stochastically dispersed within a single polymer chain. Random copolymer synthesis may proceed with a ratio of functional handle monomer units to vinylferrocene monomer units of about 1:100, 1:100, 1:10,000, or another ratio. In general, a specific ratio may be selected to achieve a balance between making functional handles available in sufficient numbers while also preserving the structure and behavior of the electrochemically switchable hydrophilicity polymers 104. In implementations, the functional handle subunits 202 will be incorporated stochastically within the electrochemically switchable hydrophilicity polymers 104. Thus, individual electrochemically switchable hydrophilicity polymers 104 may contain different numbers of functional handle subunits 202 and the functional handle subunits 202 may be located at different locations along the lengths of the electrochemically switchable hydrophilicity polymers 104. Some electrochemically switchable hydrophilicity polymers 104 may not include any functional handle subunits 202.

Figure 3:
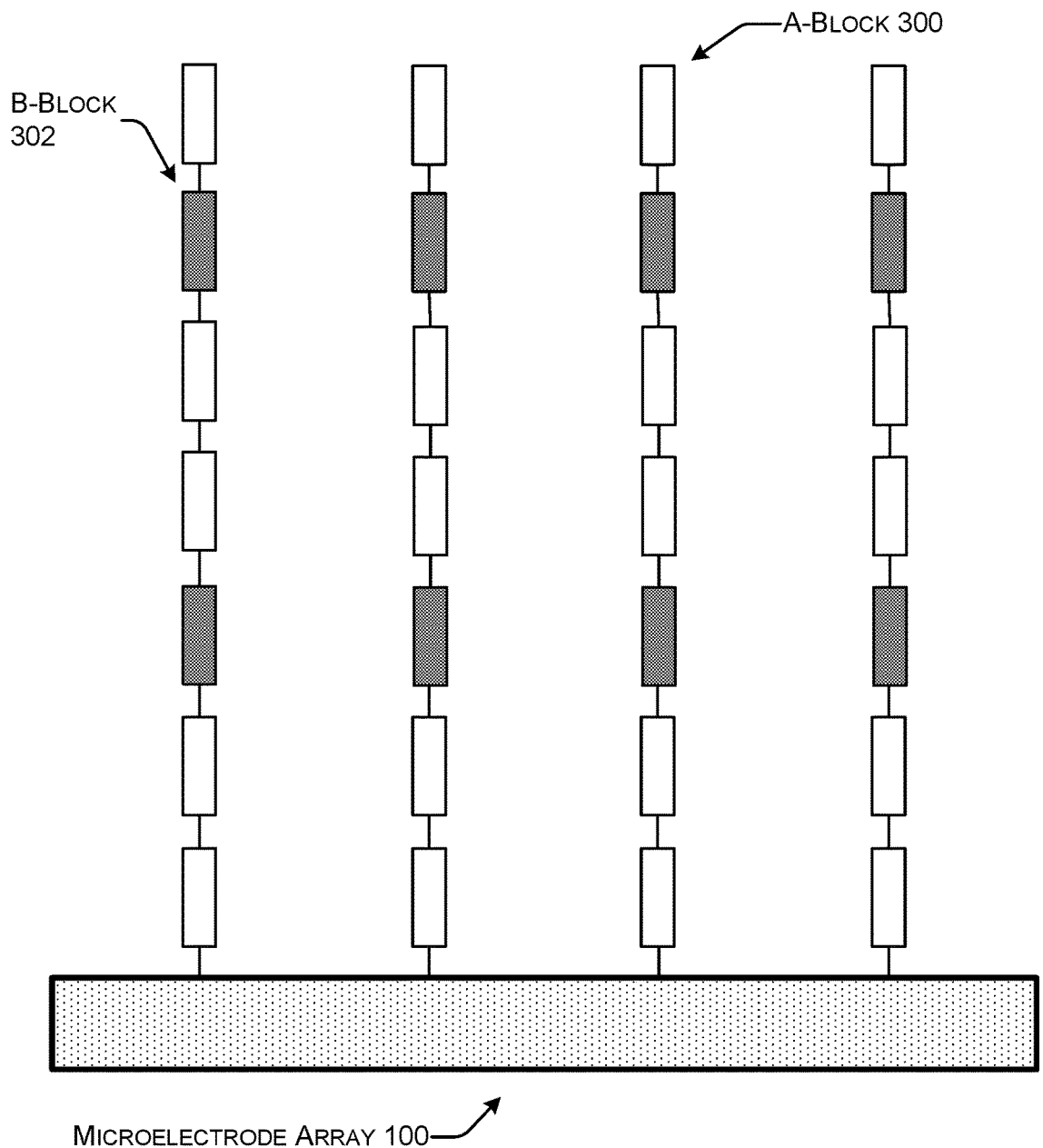
FIG. 3 is a schematic diagram of a microelectrode array coated with electrochemically switchable hydrophilicity polymers created by block copolymerization with blocks that contain functional handles.

FIG. 3 shows a microelectrode array 100 coated with electrochemically switchable hydrophilicity polymers 104 created by block copolymerization of A-blocks 300 and B-blocks 302. Block copolymers comprise two or more homopolymer subunits linked by covalent bonds. A block copolymer that includes two different homopolymer subunits may be referred to as a diblock copolymer. A block copolymer contains many constitutional units, at least one of which has a feature that is not present in the adjacent blocks. Some block copolymers may use an intermediate non-repeating subunit, known as a junction block.

In an implementation, a diblock copolymer comprised of a polyvinylferrocene A-blocks 300 and a poly(functional handle) B-blocks 302 may be employed, with the polyvinylferrocene A-block tethered to the surface. The A-blocks 300 and the B-blocks 302 will be generally arranged in a regular pattern. Each individual electrochemically switchable hydrophilic polymer 104 may have the same or substantially the same structure. The ratio of monomer subunits in the A and B-blocks may be 1:1, 10:1, 100:1, or another ratio. In general, a specific ratio may be selected to achieve a balance between making functional handles available in sufficient numbers while also preserving the structure and behavior of the electrochemically switchable hydrophilicity polymers 104.

In an implementation, a diblock copolymer comprised of a PVFc A-block 300 and a poly(acrylic acid) B-block 200 may be created by techniques similar to those used to prepare polyvinyl acetate (PVAc) and polystyrene block copolymers. Specifically, a mechanistic transformation between atom transfer radical polymerization (ATRP) and conventional radical polymerization may be used to form the block copolymers. See Hong Li et al., *Amphiphilic Block Copolymers of Polyvinyl Alcohol and Polystyrene and Their Surface Properties*, 37(11) Polymer Journal 841 (2005).

Figure 4:
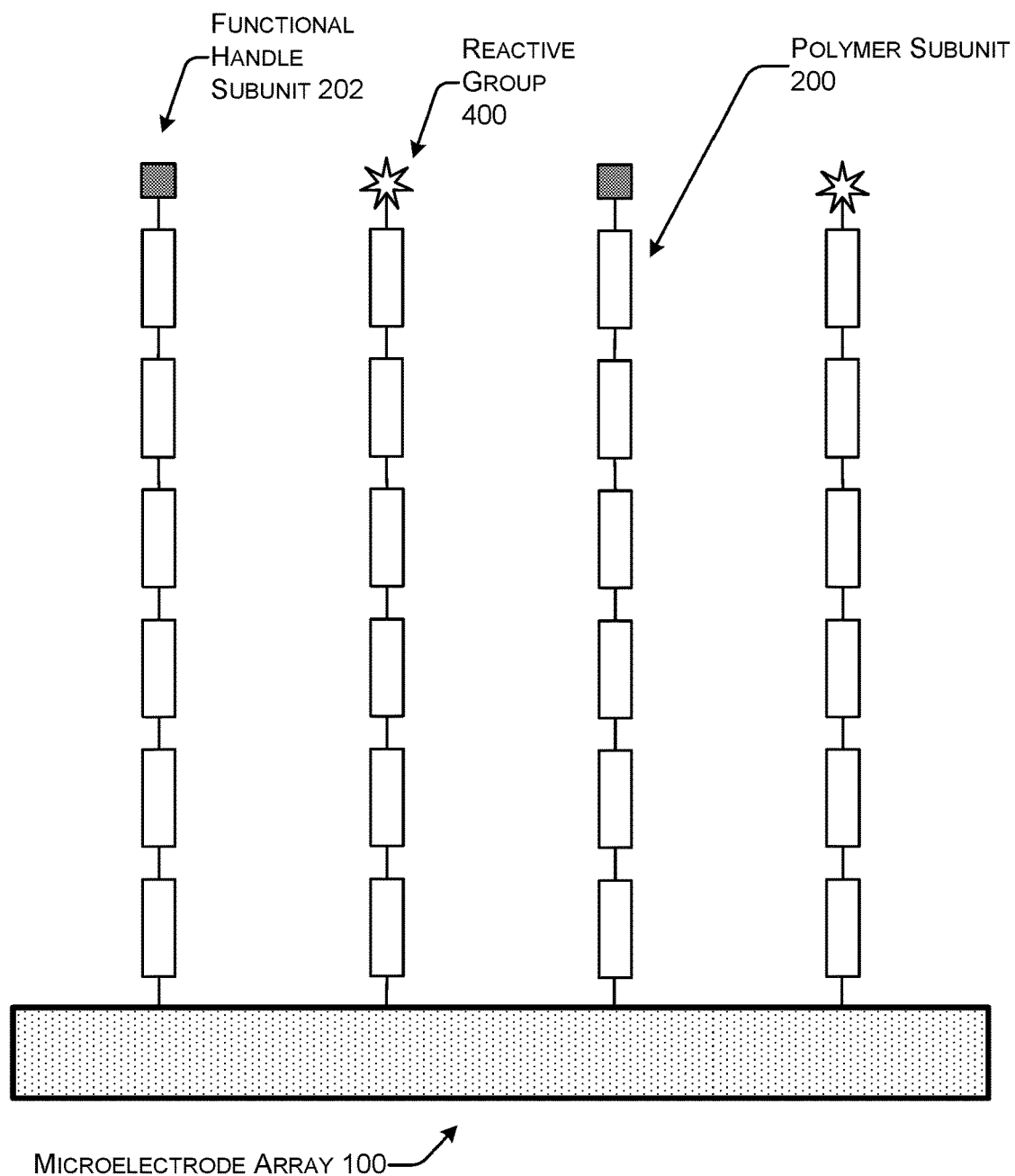
FIG. 4 is a schematic diagram of a microelectrode array coated with electrochemically switchable hydrophilicity polymers created by living polymerization and capped with a functional handle or a monomer subunit that contains a functional handle.

FIG. 4 shows a microelectrode array 100 coated with electrochemically switchable hydrophilicity polymers 104 created by living polymerization and capped with either a functional handle subunit 202 or a reactive group 400 on the free ends of the polymers. During living polymerization, an electrochemically switchable hydrophilicity polymer 104 may be capped on its free end by a polymerization reaction that adds of a functional handle unit 202 to the end of a polymer subunit. Alternatively, the electrochemically switchable hydrophilicity polymer 104 may be capped by addition of a functional handle 400 without addition of a polymer block. Either technique for capping ends further polymerization. The free end, or distal end, of an electrochemically switchable hydrophilicity polymer 104 is the end of the molecule that is not attached or anchored to the microelectrode array 100. In an implementation, the polymer subunits 200 are PVFc, the capping functional handle subunit 202 is derived from ethyl bromoacetate, and the mechanism of polymerization is ATRP.

Living polymerization is a chain polymerization technique from which chain transfer and chain termination are absent. The result is that the polymer chains grow at a more constant rate than seen in traditional chain polymerization and their lengths remain very similar. Living polymerization may be used for synthesizing block copolymers because the polymer can be synthesized in stages, each stage containing a different monomer. Living polymerization techniques include living anionic polymerization, atom transfer radical polymerization, living cationic polymerization, living ring-opening metathesis polymerization, living free-radical polymerization, and living chain-growth polycondensations. In an implementation, living anionic polymerization to generate electrochemically switchable hydrophilicity polymers 104 in which the polymer subunits 200 are PFcMA and the functional handle subunits 202 are sodium acrylate may be performed by adapting techniques described in Akira Hirao et al., *Recent advance in living anionic polymerization of functionalized styrene derivatives*, 27 Prog. Polym. Sci. 1388 (2002).

Figure 5:
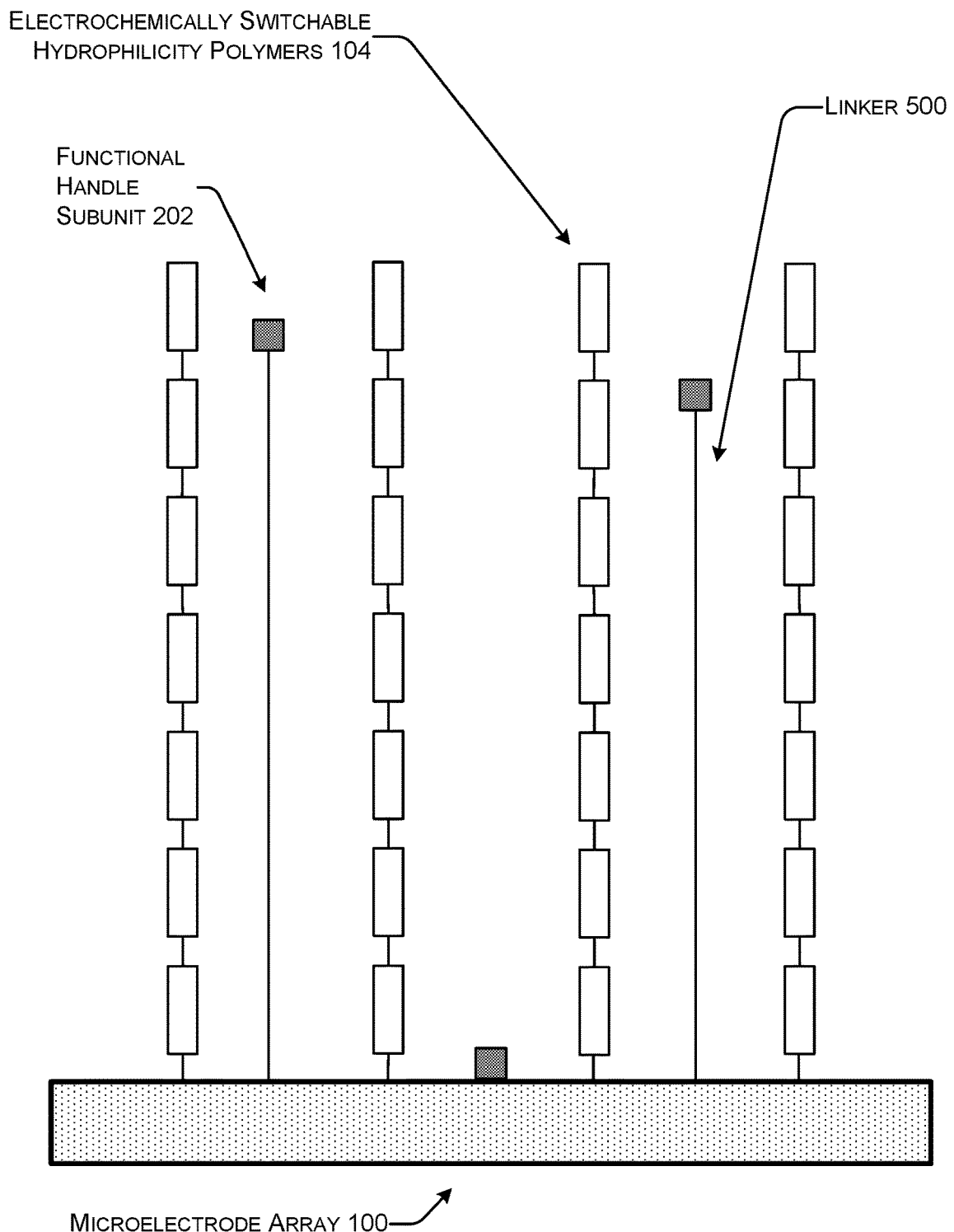
FIG. 5 is a schematic diagram of a microelectrode array coated with electrochemically switchable hydrophilicity polymers and functional handles separately attached to the surface of the microelectrode array.

FIG. 5 shows a microelectrode array 100 coated with electrochemically switchable hydrophilicity polymers 104 and functional handle subunits 202. Unlike the implementations shown in FIGS. 2-4, the functional handle subunits 202 are not included in the electrochemically switchable hydrophilicity polymers 104 but instead are to the surface of the microelectrode array 100. The functional handle subunits 202 may be attached directly to the surface of the microelectrode array 100 such as by a covalent bond formed from a portion of the function handle subunit 202 to a molecule on the surface of the microelectrode array 100. The functional handle subunits 202 may be attached to the surface of the microelectrode array 100 via a linker 500. The linker 500 may be a long, flexible molecule that is attached at one end to the functional handle subunit 202 and at the other end to the microelectrode array 100. The linker 500 may be made of PEG or similar non-reactive molecule. PEG linkers include succinimidylcarbonate-PEG, PEG-butyraldehyde, PEG-pentaldehyde, PEG-amido-propionaldehyde, PEG-urethano-propioaldehyde, and PEG-propylaldehyde.

Figure 6:
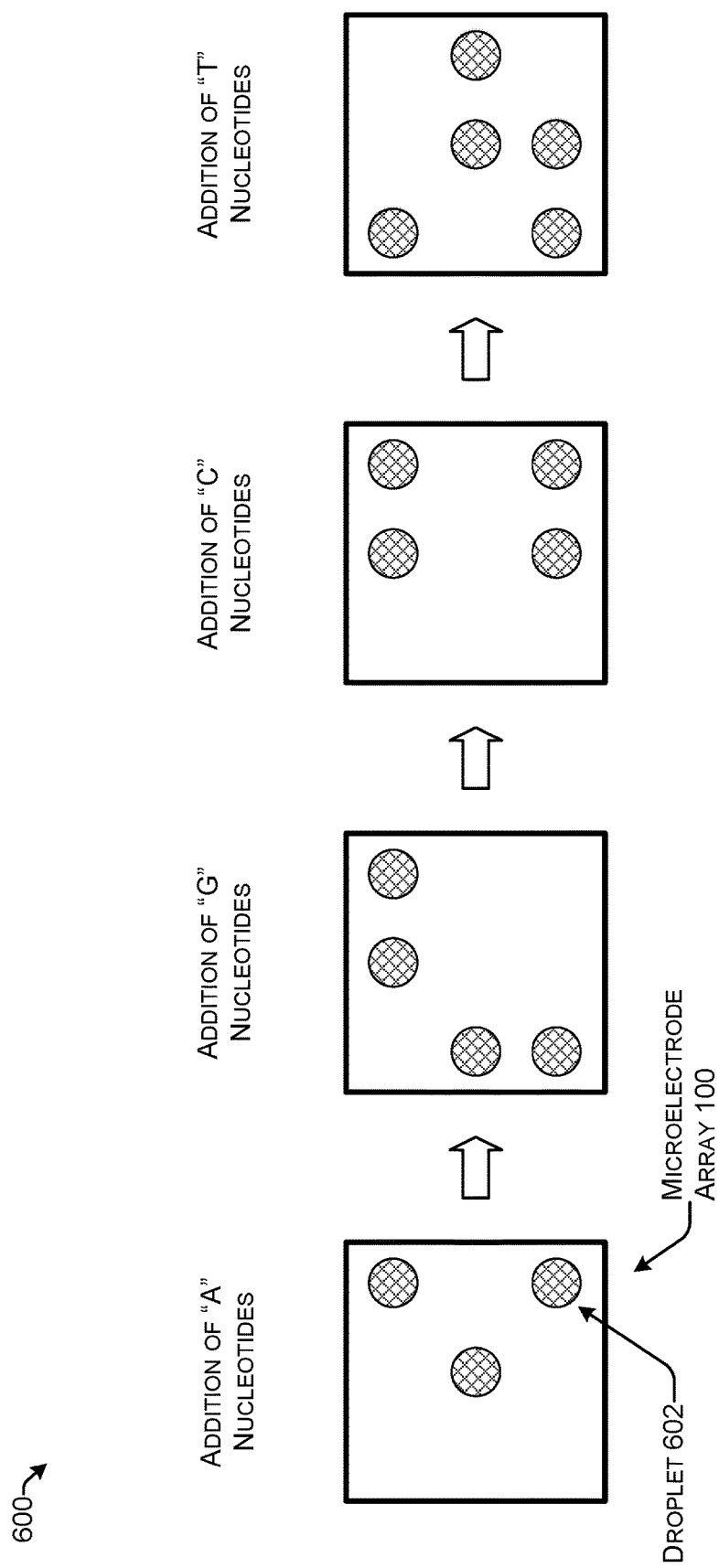
FIG. 6 is a schematic diagram of spatial control of nucleotide addition using selective hydrophilicity on the surface of a microelectrode array.

FIG. 6 is a schematic diagram 600 illustrating how changes in hydrophilicity on the surface of a microelectrode array 100 can be used to provide spatial control for solid-phase synthesis of polynucleotides. This specific example shows synthesis of polynucleotides but it is understood that this technique may be used for solid-phase synthesis of any other polymer that may be synthesized in an aqueous solution.

Polynucleotides, also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases. Nucleotides include both deoxyribonucleotides and ribonucleotides covalently linked to one or more phosphate groups. The term "polynucleotide sequence" refers to the alphabetical representation of a polynucleotide molecule. The alphabetical representation may be input and stored the memory of a computing device.

A specific, and changeable, pattern of hydrophilic regions can be created on the surface of a microelectrode array 100 coated with electrochemically switchable hydrophilicity polymers 104 such as shown in FIG. 1. Electrodes in the microelectrode array 100 are used to change the conformation of the electrochemically switchable hydrophilicity polymers 104 and switch the surface property between hydrophilic and hydrophobic. Fluid placed on the surface of the microelectrode array 100 collects at hydrophilic regions and flows off of hydrophobic regions. The fluid can form droplets 602 at multiple hydrophilic regions on the surface of the microelectrode array 100. This enables addressable, site-specific manipulations at specified locations (e.g., represented in terms of x- and y-coordinates) on the surface of the microelectrode array 100.

The hydrophilic locations may be separated from each other by hydrophobic areas to provide spatial isolation. In this example, there are nine locations or "spots" that are used for polymerization of polynucleotides. However, it is to be understood that there may be a larger number of spatially isolated and discrete locations at which nucleotides of different sequences are synthesized. All nucleotides synthesized at the same spot will generally have the same sequence. In implementations, there may be many thousands or hundreds of thousands of spots for synthesis on the surface of a microelectrode array 100. The size of a single spot can be smaller than about 1 $cm^2$, smaller than 1 $mm^2$, smaller than 0.5 $mm^2$, and in some implementations about 0.125 to 0.5 $mm^2$. This patterning of hydrophobic and hydrophilic regions creates physically isolated regions on the surface of the microelectrode array 100 without wells or other permanent structures.

The fluid contained in a droplet 602 affects the area of the microelectrode array 100 at which the droplet 602 touches. For polynucleotide synthesis, the chemicals, enzymes, or other reagents in the droplet 602 may interact with oligonucleotides incorporated into the electrochemically switchable hydrophilicity polymers 104 or otherwise attached to the surface of the microelectrode array 100 such as by any of the techniques shown in FIGS. 2-5. Thus, for polynucleotide synthesis, the oligonucleotides from which polymer synthesis begins are attached to a functional handle subunit 202. In an implementation, a 3'-hydroxyl group of an oligonucleotide may be a reactive group.

In an implementation, the droplet 602 may be a reagent solution that includes nucleotides, polymerases, metal cofactors, a buffer, and any other components needed to attach a nucleotide to the end of a growing polynucleotide strand. Nucleotides present in a droplet 602 are incorporated on the ends of oligonucleotides present on the surface of the microelectrode array 100 by the action of a polymerase. Techniques for enzymatic nucleotide synthesis are known to those of skill in the art. Some example techniques are described in U.S. patent application Ser. No. 16/563,797 filed on Sep. 6, 2020, with the title "Array-based Enzymatic Oligonucleotide Synthesis."

Although the entire surface of the microelectrode array 100 may be initially covered with the reagent solution, the reagent solution flows off of the hydrophobic regions quickly before significant nucleotide polymerization. Thus, extension of growing nucleotides occurs in the droplets 602 of reagent solution that sit on the surface of the microelectrode array 100. There is no, or essentially no, addition of nucleotides at regions of the microelectrode array 100 that are hydrophobic.

To control which nucleotide is added to the growing polynucleotides, the reagent solution may contain only a single species of nucleotide. The nucleotides that is included in the reagent solution may be changed during each cycle of synthesis. In this example, the reagent solution first contains adenine, then guanine, cytosine, and next thymine. The species of nucleotide added during a cycle controls "what" is added (e.g., A, G, C, or T) each cycle. The locations of the hydrophilic regions controls "where" addition occurs. By varying what is added and where additions occur, it is possible to synthesize a population of polynucleotides at on the surface of the solid substrate with different sequences.

In an implementation, the nucleotides may be protected nucleotides that include a blocking or protecting group which prevents the addition of more than a single nucleotide. Numerous nucleotide protecting groups are known to those of ordinary skill in the art. Some examples of protecting groups include esters, ethers, carbonitriles, phosphates, carbonates, carbamates, hydroxylamine, borates, nitrates, sugars, phosphoramide, phosphoramidates, phenylsulfenates, sulfates, sulfones, and amino acids. See Michael L. Metzker et al., *Termination of DNA Synthesis by Novel 3'-modified-deoxyribonucleoside 5'-triphosphates,* 22(20) Nucl. Acids Res., 4259 (1994) and U.S. Pat. Nos. 5,763,594, 6,232,465, 7,414,116, and 7,279,563.

Other types of protecting groups include 3'-O-amino, 3'-O-allyl, and a 3'-O-azidomethyl groups. Further examples of specific protecting groups include O-phenoxyacetyl; O-methoxyacetyl; O-acetyl; O-(p-toluene)-sulfonate; O-phosphate; O-nitrate; O-[4-methoxyl]-tetrahydrothiopyranyl; O-tetrahydrothiopyranyl; O-[5-methyl]-tetra-hydrofuranyl; O-[2-methyl,4-methoxy]-tetrahydropyranyl; O-[5-methyl]-tetrahydropyranyl; and O-tetrahydrothiofuranyl. See U.S. Pat. No. 8,133,669 for a discussion of these protecting groups. Additional examples of protecting groups are provided in U.S. patent application Ser. No. 16/230,787 filed on Dec. 21, 2018.

In such implementation, the reagent solution may contain a deblocking solution instead of nucleotides. Thus, only those locations on the surface of the microelectrode array 100 that are hydrophilic and are covered with droplets 602 containing the reagent solution will be deblocked. Once specific areas are deblocked, all of the electrochemically switchable hydrophilicity polymers 104 may be changed to a hydrophilic conformation and the entire surface of the microelectrode array 100 can be coated with a second reagent solution that contains protected nucleotides. The second reagent solution that contains protected nucleotides may contain only a single species of nucleotide. Thus, by limiting the type of nucleobase added at the deblocked locations on the surface of the microelectrode array, the sequence of the growing polynucleotide strands is controlled.

Even though the whole microelectrode array 100 is contacted with nucleotides, the nucleotides will incorporate into the growing polynucleotide strands only at the locations that have been deblocked. Incorporation of protected nucleotides adds blocking groups to the ends of any unblocked polynucleotides and the process can be repeated. The locations of deblocking and the species of protected nucleotide added can be (but are not necessarily) varied each cycle creating a population of polynucleotides with different sequences.

In this example, first adenine is added at three locations on the surface of the microelectrode array 100. Next guanine is added at four locations followed by the addition of cytosine at four locations and then thiamine at five locations. This adds each of the standard nucleotides at selected locations on the surface of the microelectrode array 100. The sequential addition of nucleotides may be repeated until all polynucleotides are fully synthesized. The order of nucleotide base addition is merely illustrative and the species of nucleotides may be added in any order.

The polynucleotide sequences created by the technique shown in FIG. 6 may be determined in advance of synthesis as with any other technique for artificial synthesis of polynucleotides. For example, the predetermined polynucleotide sequences may be manually specified by a human user or generated by a computer system.

In some implementations, the polynucleotide sequences may be used to encode digital data. The specific polynucleotide sequence of nucleotide bases (e.g., GCTAGACCT) may encode a bit sequence (e.g., 011010). Proof of concept systems and techniques for storing data in polynucleotides have been previously demonstrated. See Lee Organick et al., *Random Access in Large-Scale DNA Data Storage,* 36:3 Nat. Biotech. 243 (2018) and Christopher N. Takahashi et al., *Demonstration of End-to-End Automation of DNA Data Storage,* 9 Sci. Rep. 4998 (2019).

The polymerase used to incorporate nucleotides onto the ends of growing polynucleotides may be a DNA-dependent DNA polymerase or a template-independent polymerase. DNA-dependent DNA polymerases, also called template-dependent polymerases, require a template strand with an attached primer to initiate synthesis. There are many commercially available DNA-dependent DNA polymerases provided for use in PCR that are suitable for the techniques of this disclosure. Examples of DNA-dependent DNA polymerases include *E. coli* DNA polymerase I and its Klenow fragment, T4 DNA polymerase, native and modified T7 DNA polymerase, phi29 DNA polymerase, Bst DNA polymerase, and Taq DNA polymerase, Deep Vent® DNA Polymerase (available from New England Biolabs, Inc.), Q5® high-fidelity DNA polymerase (available from New England Biolabs, Inc.), and KAPA HiFi DNA polymerase (available from Roche Diagnostics). Characteristics and reaction conditions of the DNA-dependent DNA polymerases are known to those of skill in the art and are available from the supplier and/or presented in reference material such as Kucera, R. B. and Nichols, N. M., *DNA-Dependent DNA Polymerases*, 84 Current Protocols in Molecular Biology, 3.5.1-3.5.19 (2008).

Template independent polymerases are DNA or RNA polymerases that perform de novo oligonucleotide synthesis without use of a template strand. Currently known template-independent polymerases include TdT, poly(A) polymerase, and tRNA nucleotidyltransferase. TdT adds nucleotides indiscriminately to the 3' hydroxyl group at the 3' end of single-stranded DNA. TdT performs unregulated synthesis adding any available deoxynucleotide triphosphate (dNTP). TdT uses an existing single-stranded polynucleotide referred to as an "initiator" as the starting point for synthesis. Although TdT performs unregulated synthesis and does not require a template strand if provided with protected nucleotides TdT can be constrained to add only a single nucleotide.

Illustrative Process

For ease of understanding, the process discussed in this disclosure is delineated as separate operations represented as independent blocks. However, these separately delineated operations should not be construed as necessarily order dependent in their performance. The order in which the process is described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 7:
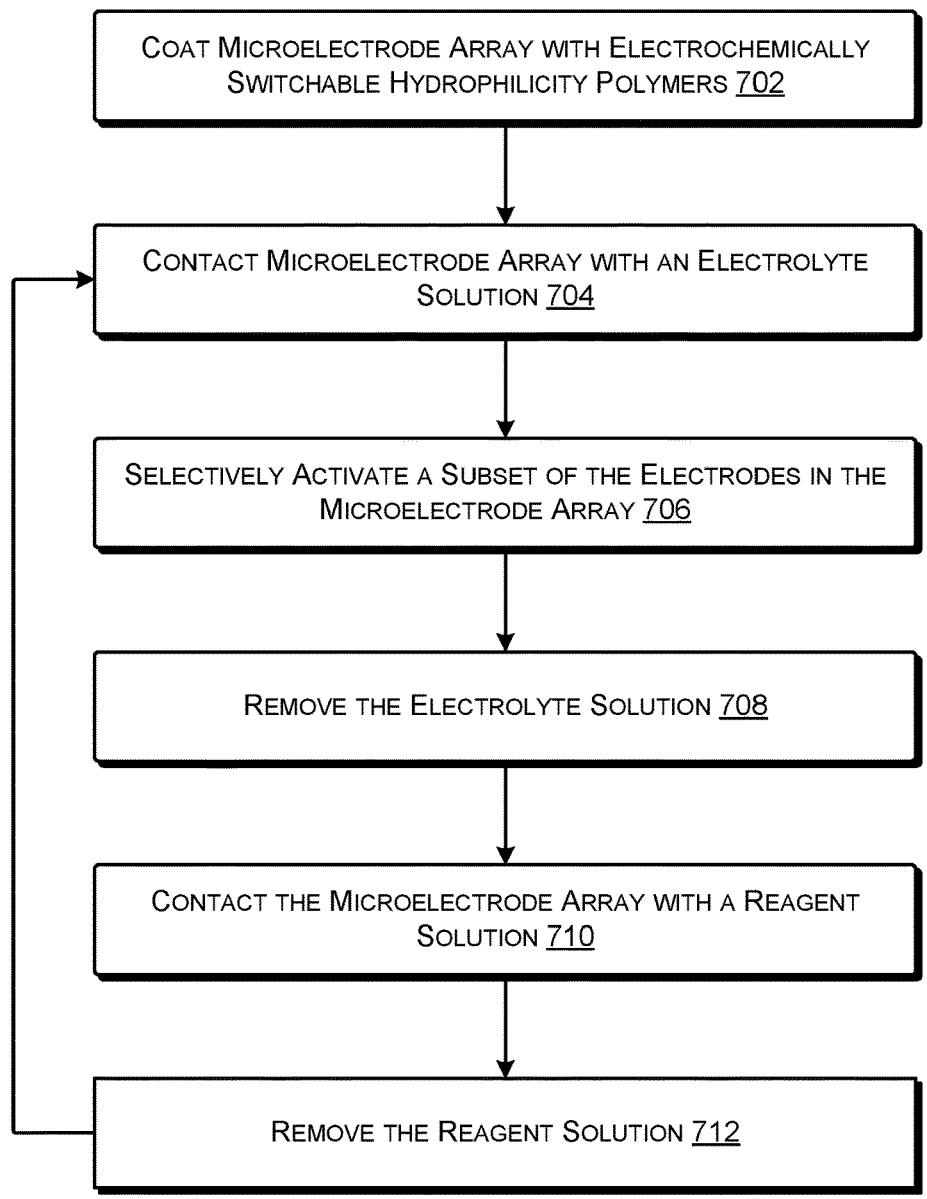
FIG. 7 is a flow diagram showing an illustrative process for solid-phase synthesis using a microelectrode array coated with electrochemically switchable hydrophilicity polymer.

FIG. 7 shows a process 700 for solid-phase synthesis with a microelectrode array coated with electrochemically switchable hydrophilicity polymers. Process 700 may be implemented, for example, using any of the microelectrode arrays shown in FIGS. 1-5, the technique shown in FIG. 6, and/or the system and computing device shown in FIGS. 8 and 9.

At operation 702, a microelectrode array is coated with electrochemically switchable hydrophilicity polymers. The electrochemically switchable hydrophilicity polymers may be attached to the surface of the microelectrode array by any conventional technique for attaching polymers to solid substrates such as surface grafting. For example, the surface of the solid substrate may be coated with polyvinylferrocene polymers such as PVFc or PFcMA. The surface of the solid substrate array may be functionalized by grafting PVFc with tetraethyl orthosilicate (TEOS) onto a silicon substrate or by SI-ATRP of FcMA monomers onto a silicon substrate. This creates a microelectrode array that is coated with a plurality of electrochemically switchable hydrophilicity polymers.

At operation 704, the microelectrode array is contacted with an electrolyte solution. The electrolyte solution is an aqueous solution that is attracted to hydrophilic regions of the microelectrode array. The microelectrode array may be flooded with the electrolyte solution or submerged into the electrolyte solution so that the entire surface of the microelectrode array including hydrophobic regions are in contact with the electrolyte solution. In implementations, the electrolyte solution may be a buffer solution. The electrolyte solution may be delivered to the surface of the microelectrode array by a manual technique such as pipetting. The electrolyte solution may also be delivered to the microelectrode array by an automated or mechanized system such as a fluidics or laboratory automation system. The ions that provide buffering may also be the electrolytes. The electrolyte solution may also be an ionic solution without buffering capacity (e.g., salt water).

At operation 706, a subset of the electrodes in the microelectrode array are selectively activated. This creates a pattern of hydrophilic regions and hydrophobic regions on the surface of the microelectrode array. Activation changes the voltage of the electrodes to positive. In some implementations, the current at the activated electrodes may be about +10 volts. The electrodes that are not activated may have a negative or neutral voltage. Activation of electrodes causes the electrochemically switchable hydrophilicity polymers at or proximate to those electrodes to change into a hydrophilic conformation. The electrolyte solution carries the current from the electrodes to the metal ions in the electrochemically switchable hydrophilicity polymers. Activation of electrodes on a dry microelectrode array (i.e., without an electrolyte or other conductive solution) may not result in changes to the hydrophilicity of the electrochemically switchable hydrophilicity polymers. Once a pattern of hydrophilic and hydrophobic regions is created, the electrodes may be turned off for the other operations in process 700.

At operation 708, the electrolyte solution may be removed. The electrolyte solution may be removed by any suitable technique for removing a liquid from the surface of a microelectrode array. For example, techniques used for drying integrated circuits during manufacturing may be adapted for drying the microelectrode array. In an implementation, the microelectrode array may be dried by spinning so that centrifugal force pulls fluid off of the surface of the microelectrode array. The microelectrode array may be spun by a motor configured to rapidly rotate the microelectrode array. In an implementation, the microelectrode array may be blown dry by movement of a gas over the surface of the microelectrode array. A gas such as air or nitrogen may be forced over the surface of the microelectrode array. The gas may be heated. During a drying step, the entire surface of the microelectrode array may be out of solution and dry.

The electrolyte solution may also be removed by displacement with another fluid. The surface of the microelectrode array may be flooded with a wash solution or a reagent solution in sufficient quantity to displace the electrolyte solution. The microelectrode array may also be dipped into another solution. Thus, the electrolyte solution can be replaced by a different solution without drying of the surface of the microelectrode array.

At operation 710, the microelectrode array is contacted with a reagent solution. The reagent solution may be flowed across the surface of the microelectrode array. The reagent solution will follow the wettability gradient created by the electrochemically switchable hydrophilicity polymers and collect or form droplets on the hydrophilic regions of the microelectrode array. The reagent solution will generally not be present on the hydrophobic regions of the microelectrode array.

The reagent solution may contain a chemical, compound, or material that attaches to a functional group (or to a monomer previously added to a functional group) and remains bound to the surface of the microelectrode array. The reagent solution may contain monomer subunits of a type of polymer that is being synthesized by solid-phase synthesis on the microelectrode array. In an implementation, the polymer may be a polynucleotide and the monomer subunits may be nucleotides such as dNTPs. In an implementation, the polymer may be a polypeptide and the monomer subunits may be peptides. Other types of polymers may also be synthesized by process 700. The reagent solution may also contain other reagents or components in addition to monomer subunits. For example, the reagent solution may contain enzymes (e.g., polymerase, ligase, etc.), metal co-factors, deblocking agents, buffers, and the like. The components of a reagent solution will depend on the type of polymer being synthesized and the specific synthetic technique.

In an implementation, the reagent solution may provide biological material rather than chemical. For example, process 700 and other techniques provided in this disclosure may be used for tissue printing, three-dimensional bioprinting, cell patterning, implementing biomedical microelectromechanical systems (bioMEMS), or creating organs-on-chips (OOC). All of these and related techniques involve patterning cells or other biological material such as biolinks on to a substrate. Biolinks are liquid mixtures of cells, matrix, and nutrients.

There are various techniques known to those of ordinary skill in the art for creating structures of biological materials such as inkjet cell printing, optical and optoelectronic tweezers, laser-based cell patterning, acoustic force patterning, electrokinetic forces (dielectrophoresis), magnetic bioprinting, photolithography, stereolithography, chemical patterning, microcontact printing, and direct cell extrusion. See Adrian Martinez-Rivas et al., *Methods of Micropatterning and Manipulation of Cells for Biomedical Applications,* 8 Micromachines 347 (2017). Persons of ordinary skill in the art will understand how to adapt existing tissue printing, cell patterning and other similar techniques to use the systems and methods of this disclosure for controlling the spatial location of biological material addition. Tissue printing and similar applications that deposit biological material may be performed using a microelectrode array and electrochemically switchable hydrophilicity polymers without functional handles.

At operation 712, the reagent solution is removed. The reagent solution may be allowed to equilibrate on the surface of the microelectrode array for a predetermined time. During this time polymerization or other reactions such as deblocking will occur. Removal of the reagent solution may be performed by any of the techniques described at operation 708 for removal of the electrolyte solution.

In an implementation, the reagent solution may be removed by contacting the microelectrode array with a wash solution and activating the electrodes of the microelectrode array. All or substantially all of the electrodes may be activated to make the entire surface of the microelectrode array hydrophilic. Without being bound by theory, it is believed that washing the electrochemically switchable hydrophilicity polymers when in a hydrophilic conformation rather than a hydrophobic conformation will allow an aqueous solution to better penetrate in between the individual polymers and clean the surface. The wash solution may be the same as the electrolyte solution. In an implementation, the reagent solution may be removed by addition of the electrolyte solution. Thus, the reagent solution may be used as a wash solution. Also, the buffer or other solution used to create the reagent solution absent any specific reagents may be used as the wash solution.

After removal of the reagent solution, process 700 may return to operation 704 where the microelectrode array is again contacted with an electrolyte solution and the pattern of hydrophobic regions and hydrophilic regions is reset. The process 700 may repeat multiple times. During each round or iteration, the subset of the electrodes that are activated may change. This may result in different regions of the microelectrode array being hydrophilic and holding the reagent solution during each round of synthesis. Thus, activation of the electrodes through control of hydrophilicity controls the locations of site-selective addition of monomers to growing polymer strands. The contents of the reagent solution may also be varied each round. However, either or both the location of electrode activation and the contents of the reagent solution may remain constant over multiple rounds of synthesis. If the reagent solution contains only a single type of monomer subunit (e.g., a single species of nucleotide) then the particular species of monomer incorporated each round may also change. FIG. 6 shows an example pattern of adding different monomers at different locations on the surface of a microelectrode array during multiple rounds of synthesis.

Illustrative System and Computer Architecture

Figure 8:
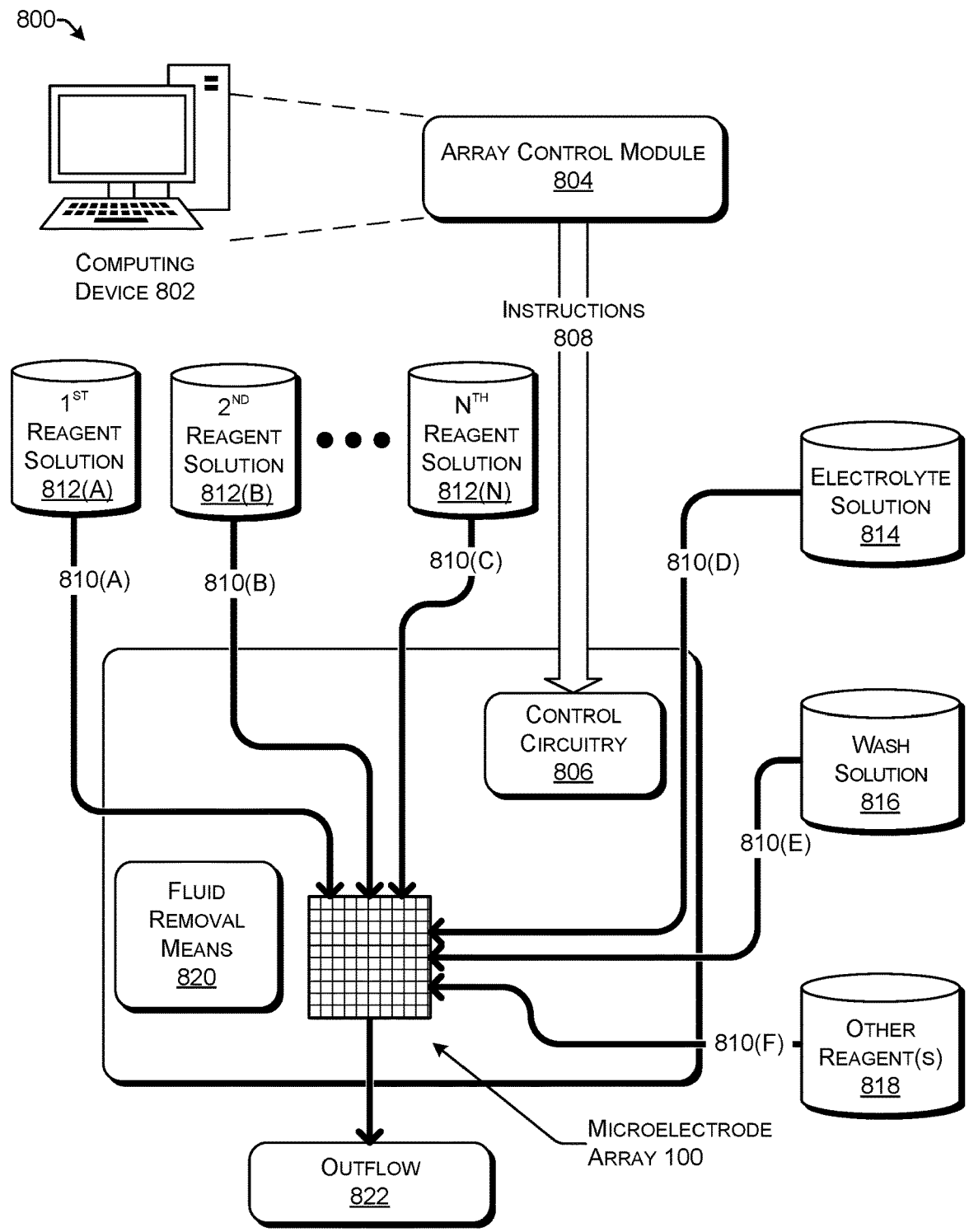
FIG. 8 is an illustrative system for solid-phase synthesis using a microelectrode array coated with electrochemically switchable hydrophilicity polymers.

FIG. 8 shows an illustrative system 800 that may include a computing device 802 with an array control module 804 that is communicatively connected to control circuitry 806 that controls activation of individual electrodes in the microelectrode array 100. The computing device 802 may be implemented as any type of conventional computing device such as a desktop computer, a laptop computer, a server, a hand-held device, or the like. In an implementation, the computing device 802 may be a part of a device that houses the microelectrode array 100 rather than a separate device. The control circuitry 806 may be implemented as any type of circuitry suitable for controlling hardware devices such as a printed circuit board, microcontroller, a programmable logic controller (PLC), or the like. The control circuitry 806 receives instructions 808 provided by the array control module 804.

As described above, the microelectrode array 100 includes a plurality of electrodes that can be independently activated to vary the charge across the surface of the microelectrode array 100. The microelectrode array 100 may be located within a reaction chamber or container capable of maintaining an aqueous or predominantly aqueous environment in contact with the surface of the microelectrode array 100. The reaction chamber may be a closed chamber that encases the microelectrode array 100. The reaction chamber may be open such as walls or barriers surrounding the edges of the microelectrode array 100 that prevent fluid from readily flowing off the surface of the microelectrode array 100.

The array control module 804 may provide instructions 808 that control the microelectrode array 100. The instructions 808 may cause the microelectrode array 100 to activate specific patterns of electrodes in a specific temporal sequence. Thus, the control circuitry 806 may be able to independently control the voltage at each of the electrodes in the microelectrode array 100. The control circuitry 806 may also be able to activate fluid delivery pathways 810 that control the movement of fluids to the surface of the microelectrode array 100. The fluid delivery pathways 810 may be implemented by tubes and pumps, automated fluidic systems, laboratory robotics, or other techniques known to those of ordinary skill in the art. The instructions 808 may indicate predetermined sequences of polynucleotides or other polymers that are to be synthesized on the microelectrode array 100. Interpretation and implementation of the instructions 808 results in coordinated activation of specific electrodes and opening of specific fluid delivery pathways 810 that causes the system 800 to synthesize polynucleotides or other polymers with predetermined sequences.

In an implementation, the system 800 may include vessels or containers that hold one or more reagent solutions 812 (e.g., first reagent solution 812(A), second reagent solution 812(B), . . . , Nth reagent solution 812(N)). The reagent solution 812 may contain a chemical, compound, or material that attaches to a functional group (or to a monomer previously added to a functional group) and remains bound to the surface of the microelectrode array 100. The reagent solution 812 may contain monomer subunits of a type of polymer that is being synthesized by solid-phase synthesis on the microelectrode array 100. In an implementation, the polymer may be a polynucleotide and the monomer subunits may be nucleotides such as dNTPs. In an implementation, the polymer may be a polypeptide and the monomer subunits may be peptides. The reagent solution 812 may also contain other reagents or components in addition to monomer subunits. For example, the reagent solution may contain enzymes (e.g., polymerase, ligase, etc.), metal co-factors, deblocking agents, buffers, and the like. The components of a reagent solution will depend on the type of polymer being synthesized and the specific synthetic technique.

In an implementation for polynucleotide synthesis, the reagent solutions 812 may each include a different species of nucleotide. Thus, there may be four reagents solutions that each contain one type of nucleotide (i.e., A, G, C, or T/U). The containers holding the reagent solutions 812 may be connected to the microelectrode array 100 by respective fluid delivery pathways 810(A), 810(B), and 810(C). In an implementation, activation or opening of a fluid delivery pathway 810 may cause a gentle laminar flow of a reagent solution 812 over the surface of the microelectrode array 100. In an implementation, activation of a fluid delivery pathway 810 may add a reagent solution 812 to a reaction vessel containing the microelectrode array 100. Sufficient fluid may be added to submerge the microelectrode array 100 in the reagent solution 812. In an implementation, activation of a fluid delivery pathway 810 may cause the microelectrode array 100 to be physically moved into one of a vessel or container that holds a reagent solution 812.

In an implementation, the reagent solution 812 may provide biological material rather than chemical. For example, the system 800 may be used for tissue printing, three-dimensional bioprinting, cell patterning, implementing biomedical microelectromechanical systems (bioMEMS), or creating organs-on-chips (OOC). All of these and related techniques involve patterning cells or other biological material such as biolinks on to a substrate. Biolinks are liquid mixtures of cells, matrix, and nutrients. For example, each of multiple different types of reagent solutions 812(A)-812(N) may contain different types of cells.

One or more of the electrolyte solution 814, a wash solution 816, and other reagent(s) 818 may also be available in separate containers or vessels. These solutions may be delivered to the microelectrode array 100 by respective fluid delivery pathways 810(D), 810(E), and 810(F). The electrolyte solution 814 is an aqueous solution. In implementations, the electrolyte solution may be a buffer solution. The ions that provide buffering may also be the electrolytes. The electrolyte solution may also be an ionic solution without buffering capacity (e.g., salt water).

The wash solution 816 may be water or a wash buffer. The wash solution 816 may be any one of several aqueous buffers such as, for example, phosphate-buffered saline (PBS). PBS is a water-based salt solution containing disodium hydrogen phosphate, sodium chloride, and, in some formulations, may also include one or more of potassium chloride and potassium dihydrogen phosphate. Other examples of aqueous buffers known to those of ordinary skill in the art include HEPES, MOPS, PBS, PBST, TAE, TBE, TBST, TE, and TEN. See Vincent S. Stoll & John S. Blanchard, *Buffers: Principles and Practice,* 182 Meth. Enzoml., 24 (1990). The wash solution 816 may be the same as the electrolyte solution 814. One of the reagent solutions 812 may be used as the wash solution 816. Thus, in some implementations, the system 800 may omit a separate wash solution 816. Also, the buffer or other solution used to create a reagent solution 812 absent any specific reagents may be used as the wash solution 816.

The system 800 also includes a fluid removal means 820 that is implemented by one or more devices which removing fluids from the surface of the microelectrode array 100. In an implementation, the fluid removal means 820 may include a spinner. The spinner may include a motor, gears, or other mechanism to rotate the microelectrode array 100 in a circular manner such that centrifugal force pulls any fluids off of the surface of the microelectrode array 100. The utilization of rotary or spin devices to dry semiconductor wafers are well known in the art. Any of those techniques or devices may be adapted for drying the microelectrode array 100. See, for example, U.S. Pat. Nos. 4,489,501, 4,677,759, and 4,525,938. Fluids removed from the surface of the microelectrode array 100 may be captured in an outflow 822. Contents of the outflow 822 may be discarded or recycled and reused.

In an implementation, the fluid removal means 820 may include a blower. The blower forces a gas over the surface of the microelectrode array 100. Examples of blowers include nitrogen guns such as those used for drying semiconductor wafers. The gas may be air, nitrogen, or another non-reactive gas. The gas may be dried and/or heated.

In an implementation, the fluid removal means 820 is one or more of the fluid delivery pathway 810 such as the fluid delivery pathway 810(E) for the wash solution 816. Addition of another fluid to the surface of the microelectrode array 100 displaces and removes the fluid previously in contact with the microelectrode array 100. The fluid that is removed and any excess of the added fluid may be captured in the outflow 822.

In an implementation, a vacuum may be used as the fluid removal means 820 to draw fluid off of the surface of the microelectrode array 100 by negative pressure. The vacuum may create a negative pressure in a closed reaction chamber that contains the microelectrode array 100. Fluid on the surface of the microelectrode array 100 moves toward the vacuum and off of the surface of the microelectrode array 100. In an implementation, negative pressure created by the vacuum may draw in air from the surrounding environment.

Figure 9:
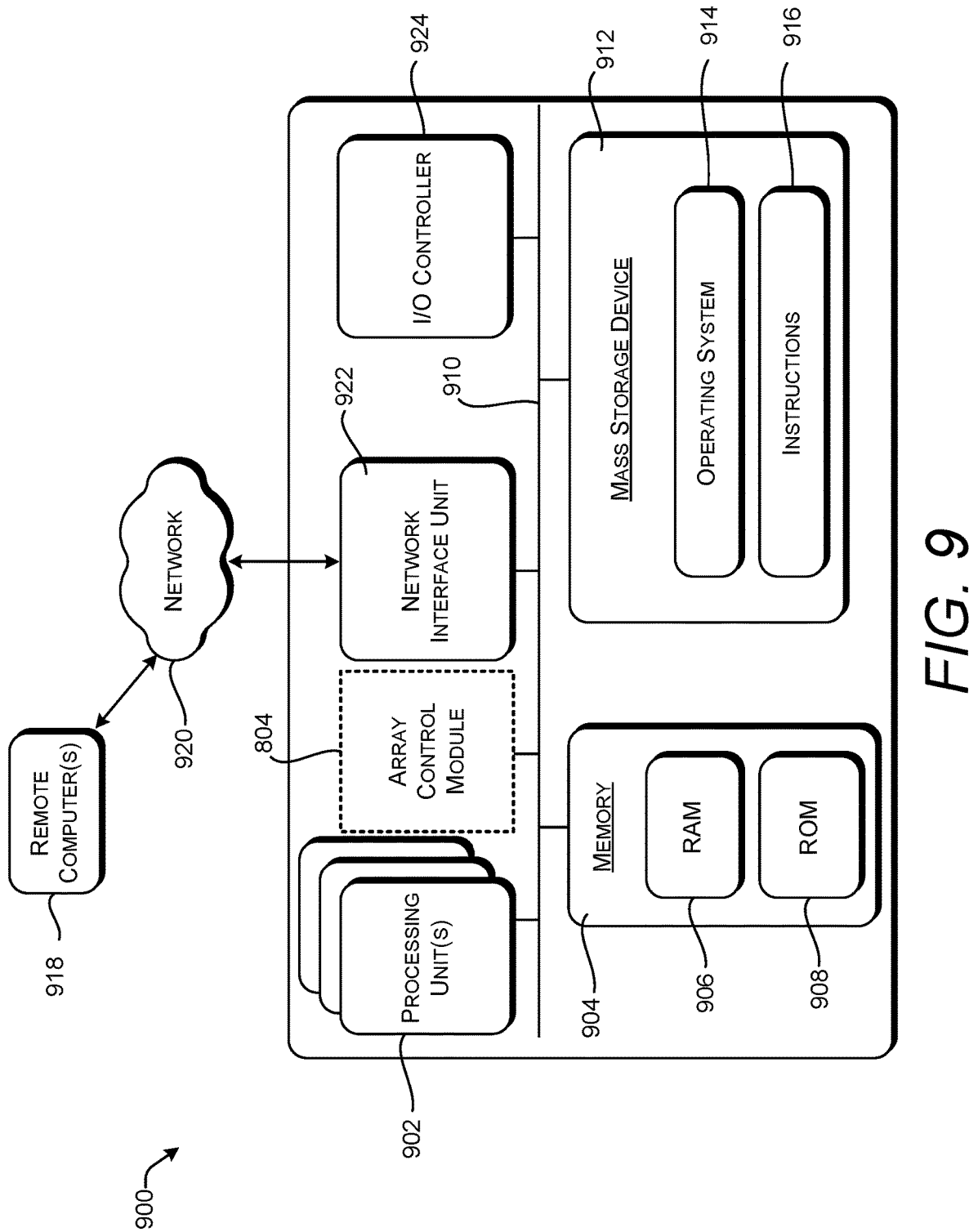
FIG. 9 is an illustrative computer architecture for implementing techniques of this disclosure.

FIG. 9 is a computer architecture diagram showing an illustrative computer hardware and software architecture for a computing device such as the computing device 802 introduced FIG. 8. In particular, the computer 900 illustrated in FIG. 9 can be utilized to implement the array control module 804.

The computer 900 includes one or more processing units 902, a system memory 904, including a random-access memory 906 ("RAM") and a read-only memory ("ROM") 908, and a system bus 910 that couples the memory 904 to the processing unit(s) 902. A basic input/output system ("BIOS" or "firmware") containing the basic routines that help to transfer information between elements within the computer 900, such as during startup, can be stored in the ROM 908. The computer 900 further includes a mass storage device 912 for storing an operating system 914 and other instructions 916 that represent application programs and/or other types of programs such as, for example, instructions to implement the synthesizer control module 604. The mass storage device 912 can also be configured to store files, documents, and data.

The mass storage device 912 may be connected to the processing unit(s) 902 through a mass storage controller (not shown) connected to the bus 910. The mass storage device 912 and its associated computer-readable media provide non-volatile storage for the computer 900. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 900.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules or other data. For example, computer-readable storage media includes, but is not limited to, RAM 906, ROM 908, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 900. For purposes of the claims, the phrase "computer-readable storage medium," and variations thereof, does not include waves or signals per se or communication media.

According to various configurations, the computer 900 can operate in a networked environment using logical connections to the remote computer(s) 918 through a network 920. The computer 900 can connect to the network 920 through a network interface unit 922 connected to the bus 910. It should be appreciated that the network interface unit 922 can also be utilized to connect to other types of networks and remote computer systems. The computer 900 can also include an input/output controller 924 for receiving and processing input from several other devices, including a keyboard, mouse, touch input, or an electronic stylus (not shown). Similarly, the input/output controller 924 can provide output to a display screen or other type of output device (not shown).

It should be appreciated that the software components described herein, when loaded into the processing unit(s) 902 and executed, can transform the processing unit(s) 902 and the overall computer 900 from a general-purpose computing device into a special-purpose computing device customized to facilitate the functionality presented herein. The processing unit(s) 902 can be constructed from any number of transistors or other discrete circuit elements, which can individually or collectively assume any number of states. More specifically, the processing unit(s) 902 can operate as a finite-state machine, in response to executable instructions contained within the software modules disclosed herein. These computer-executable instructions can transform the processing unit(s) 902 by specifying how the processing unit(s) 902 transitions between states, thereby transforming the transistors or other discrete hardware elements constituting the processing unit(s) 902.

Encoding the software modules presented herein can also transform the physical structure of the computer-readable media presented herein. The specific transformation of the physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 900 to store and execute the software components presented herein. It also should be appreciated that the architecture shown in FIG. 9 for the computer 900, or a similar architecture, can be utilized to implement many types of computing devices such as desktop computers, notebook computers, servers, supercomputers, gaming devices, tablet computers, and other types of computing devices known to those skilled in the art. For example, the computer 900 may be wholly or partially integrated into the system 900. It is also contemplated that the computer 900 might not include all of the components shown in FIG. 9, can include other components that are not explicitly shown in FIG. 9, or can utilize an architecture completely different than that shown in FIG. 9.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A microelectrode array (100) coated with electrochemically switchable hydrophilicity polymers (102).

Clause 2. The microelectrode array of clause 1, wherein the microelectrode array comprises a silicon dioxide wafer.

Clause 3. The microelectrode array of clause 1 or 2, wherein the microelectrode array comprises a complementary semiconductor-metal-oxide (CMOS) microelectrode array.

Clause 4. The microelectrode array of any of clauses 1-3, wherein the electrochemically switchable hydrophilicity polymers comprise ferrocene polymers.

Clause 5. The microelectrode array of clause 4, wherein the ferrocene polymers are at least one of polyvinylferrocene (PVFc) or poly(2-(methacryloyloxy)ethyl ferrocenecarboxylate) (PFcMA).

Clause 6. The microelectrode array of any of clauses 1-5, wherein the electrochemically switchable hydrophilicity polymers comprise functional handles.

Clause 7. The microelectrode array of claim 6, wherein the function handles comprise oligonucleotides.

Clause 8. The microelectrode array of any of clauses 6-7, wherein the functional handles are present at multiple locations throughout the length of the electrochemically switchable hydrophilicity polymers.

Clause 9. The microelectrode array of any of clauses 6-7, the functional handles are present at the free ends of the electrochemically switchable hydrophilicity polymers.

Clause 10. The microelectrode array of any of clauses 1-5, further comprising functional handles attached directly to the surface of the microelectrode array or attached to the surface of the microelectrode array a linker molecule.

Clause 11. A method comprising: contacting a microelectrode array (100) coated with electrochemically switchable hydrophilicity polymers (104) with an electrolyte solution (714); selectively activating a subset of electrodes (102) in the microelectrode array (100); removing the electrolyte solution (714); contacting the microelectrode array (100) with a reagent solution (72); removing the reagent solution (712); and repeating steps a-e.

Clause 12. The method of clause 11, wherein removing the reagent solution comprises contacting the microelectrode array with a wash solution and activating the electrodes of the microelectrode array.

Clause 13. The method of clause 10 or 11, wherein electrochemically switchable hydrophilicity polymers comprise functional handles.

Clause 14. The method of any of clauses 11-13, wherein the reagent solution comprises monomers that are polymerized onto the functional handles.

Clause 15. The method of any of clauses 11-14, wherein the functional handles comprise oligonucleotides and the monomers comprise nucleotides.

Clause 16. The method of any of clauses 11-15, wherein during a round of repeating steps a-e, the subset of electrodes is changed or a component of the reagent solution is changed.

Clause 17. The method of any of clauses 11-16, further comprising coating the microelectrode array with the electrochemically switchable hydrophilicity polymers.

Clause 18. The method of clause 17, wherein coating the microelectrode array with the electrochemically switchable hydrophilicity polymers comprises block copolymer synthesis of the electrochemically switchable hydrophilicity polymers with blocks containing functional handles.

Clause 19. The method of clause 17, wherein coating the microelectrode array with the electrochemically switchable hydrophilicity polymers comprises adding functional handles to the free ends of the electrochemically switchable hydrophilicity polymers by living polymer synthesis.

Clause 20. A system comprising: a microelectrode array (100) coated with electrochemically switchable hydrophilicity polymers (104); a first fluid delivery pathway (710(D)) configured to deliver an electrolyte solution (714) to the surface of the microelectrode array (100); a second fluid delivery pathway (710(A)) configured to deliver a reagent solution (712(A)) to the surface of the microelectrode array (100); a fluid removal means (720) for removing fluid from the surface of the microelectrode array (100); and control circuitry (706) configured to selectively activate a subset of electrodes (102) in the microelectrode array (100) and to selectively open the first fluid delivery pathway (710(D)) and the second fluid delivery pathway (712(A)).

Clause 21. The system of clause 20, further comprising: a third fluid delivery pathway configured to deliver a second reagent solution to the surface of the microelectrode array; and a computing system communicatively coupled to the control circuitry and configured to sequentially activate different subsets of electrodes and sequentially open the second fluid delivery pathway and the third fluid delivery pathway according to a preprogrammed sequence.

Clause 22. A method comprising: coating a substrate (e.g., array of resistors) with thermoresponsive polymers (e.g., poly(N-isopropylacrylamide or poly(uracilacrylate)) and functional groups (e.g., short oligonucleotides); contacting the substrate with an enzyme mixture that modifies the available functional groups (e.g., a polymerase and free nucleotide); selectively changing the temperature at a subset of locations on the surface of the substrate; (e.g., by activating resistors in the array, laser, microwaves, ultrasound) and washing the surface of the substrate at a temperature at which the thermoresponsive polymers are hydrophilic.

Clause 23. A method comprising: coating a substrate with photoresponsive polymers (e.g., spiropyran polymers or azobenzene polymers) and functional groups (e.g., acrylic acid); selectively exposing a portion of the substrate to a specific wavelength of light (e.g., 365 nm by a photomask or digital micro mirror); contacting the substrate with a reagent solution (e.g., a polymerase and free nucleotide); removing the reagent solution; contacting the substrate with a wash solution; and removing the wash solution.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A microelectrode array coated with electrochemically switchable hydrophilicity polymers, wherein the electrochemically switchable hydrophilicity polymers comprise functional handles comprising oligonucleotides that are present at multiple locations throughout the length of the electrochemically switchable hydrophilicity polymers.

2. The microelectrode array of claim 1, wherein the microelectrode array comprises a complementary semiconductor-metal-oxide (CMOS) microelectrode array.

3. The microelectrode array of claim 1, wherein the electrochemically switchable hydrophilicity polymers comprise ferrocene polymers.

4. The microelectrode array of claim 3, wherein the ferrocene polymers are at least one of polyvinylferrocene (PVFc) or poly(2-(methacryloyloxy)ethyl ferrocenecarboxylate) (PFcMA).

5. The microelectrode array of claim 1, wherein the functional handles are present at the free ends of the electrochemically switchable hydrophilicity polymers.

6. The microelectrode array of claim 1, further comprising functional handles attached directly to the surface of the microelectrode array or attached to the surface of the microelectrode array a linker molecule.

7. The microelectrode array of claim 1, wherein the functional handle subunits are incorporated stochastically within the electrochemically switchable hydrophilicity polymers.

8. The microelectrode array of claim 1, wherein the functional handles are attached to the surface of the microelectrode array by covalent bond formed from a portion of the functional handle subunit to a molecule on the surface of the microelectrode array.

9. A method comprising:
a. contacting a microelectrode array coated with electrochemically switchable hydrophilicity polymers with an electrolyte solution, wherein the electrochemically switchable hydrophilicity polymers comprise functional handles comprising oligonucleotides that are present at multiple locations throughout the length of the electrochemically switchable hydrophilicity polymers;
b. selectively activating a subset of electrodes in the microelectrode array;
c. removing the electrolyte solution;
d. contacting the microelectrode array with a reagent solution;
e. removing the reagent solution; and
f. repeating steps a-e.

10. The method of claim 9, wherein removing the reagent solution comprise s contacting the microelectrode array with a wash solution and activating the electrodes of the microelectrode array.

11. The method of claim 9, wherein the reagent solution comprises monomers that are polymerized onto the functional handles.

12. The method of claim 11, wherein the monomers comprise nucleotides.

13. The method of claim 9, wherein during a round of repeating steps a-e, the subset of electrodes is changed or a component of the reagent solution is changed.

14. The method of claim 9, further comprising coating the microelectrode array with the electrochemically switchable hydrophilicity polymers.

15. The method of claim 14, wherein coating the microelectrode array with the electrochemically switchable hydrophilicity polymers comprises block copolymer synthesis of the electrochemically switchable hydrophilicity polymers with blocks containing functional handles.

16. The method of claim 14, wherein coating the microelectrode array with the electrochemically switchable hydrophilicity polymers comprises adding functional handles to the free ends of the electrochemically switchable hydrophilicity polymers by living polymer synthesis.

17. A system comprising:
a microelectrode array coated with electrochemically switchable hydrophilicity polymers, wherein the electrochemically switchable hydrophilicity polymers comprise functional handles comprising oligonucleotides that are present at multiple locations throughout the length of the electrochemically switchable hydrophilicity polymers;
a first fluid delivery pathway configured to deliver an electrolyte solution to the surface of the microelectrode array;
a second fluid delivery pathway configured to deliver a reagent solution to the surface of the microelectrode array;
a fluid removal means for removing fluid from the surface of the microelectrode array; and
control circuitry configured to selectively activate a subset of electrodes in the microelectrode array and to selectively open the first fluid delivery pathway and the second fluid delivery pathway.

18. The system of claim 17, further comprising:
a third fluid delivery pathway configured to deliver a second reagent solution to the surface of the microelectrode array; and
a computing system communicatively coupled to the control circuitry and configured to sequentially activate different subsets of electrodes and sequentially open the second fluid delivery pathway and the third fluid delivery pathway according to a preprogrammed sequence.

* * * * *